Figure 1:
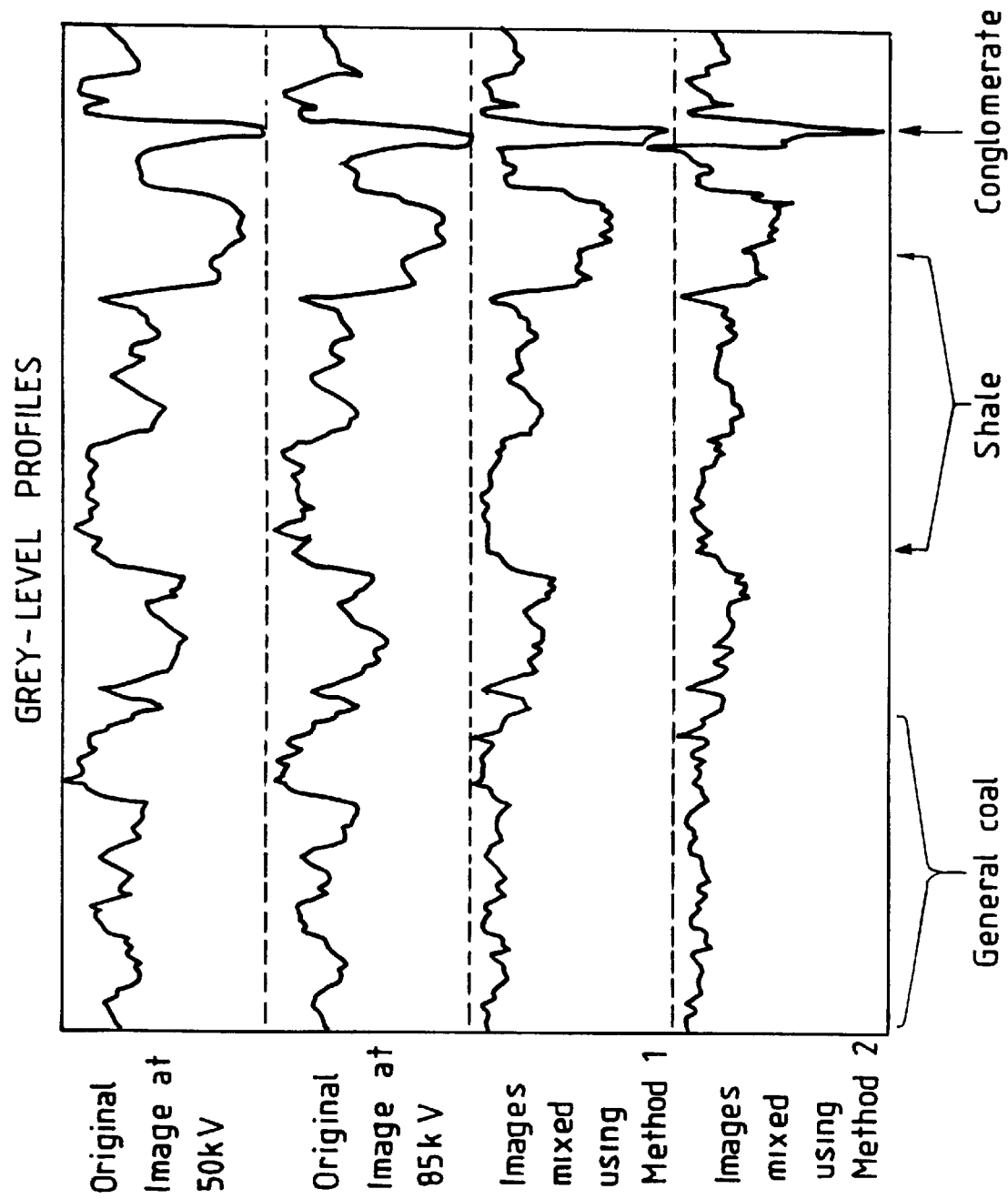

United States Patent [19]
Pidcock

[11] Patent Number: 6,122,343
[45] Date of Patent: Sep. 19, 2000

[54] METHOD AND AN APPARATUS FOR ANALYZING A MATERIAL

[75] Inventor: Andrea Gabrielle Pidcock, Western Australia, Australia

[73] Assignee: Technological Resources Pty Limited, Victoria, Australia

[21] Appl. No.: 08/930,752

[22] PCT Filed: Apr. 4, 1996

[86] PCT No.: PCT/AU96/00207

§ 371 Date: Feb. 23, 1998

§ 102(e) Date: Feb. 23, 1998

[87] PCT Pub. No.: WO96/31770

PCT Pub. Date: Oct. 10, 1996

[30] Foreign Application Priority Data

Apr. 7, 1995 [AU] Australia .................................. PN2262

[51] Int. Cl.$^7$ .................................................. G01N 23/06
[52] U.S. Cl. ................................ 378/53; 378/51; 209/589
[58] Field of Search .............................. 250/273; 378/51, 378/53, 98.9; 209/589

[56] References Cited

U.S. PATENT DOCUMENTS

| | | |
|---|---|---|
| 3,452,192 | 6/1969 | Hanken .................................. 250/43.5 |
| 4,090,073 | 5/1978 | De Villiers et al. . |
| 4,090,074 | 5/1978 | Watt et al. . |
| 4,910,758 | 3/1990 | Herrick . |

FOREIGN PATENT DOCUMENTS

| | | |
|---|---|---|
| 1 531 572 | 11/1978 | United Kingdom . |
| 2 066 456 | 7/1981 | United Kingdom . |
| 2 067 753 | 7/1981 | United Kingdom . |
| 2 083 618 | 3/1982 | United Kingdom . |
| 2 091 417 | 7/1982 | United Kingdom . |
| 2 107 861 | 5/1983 | United Kingdom . |
| 2 223 842 | 4/1990 | United Kingdom . |
| WO 88/02111 | 3/1988 | WIPO . |

*Primary Examiner*—David V. Bruce
*Assistant Examiner*—Michael J. Schwartz
*Attorney, Agent, or Firm*—Merchant & Gould P.C.

[57] ABSTRACT

A method and an apparatus for analyzing a material, such as coal and iron ore, particularly with a view to identifying contaminants, is disclosed. The method and apparatus are based on the use of multiple (particularly dual) energy x-ray analysis with x-rays at different photon energies. X-rays are transmitted through a material and the detected x-rays are processed to produce an image of the material that combines together the separated images produced by the different photon energy x-rays. The combined image has enhanced contrast which minimizes the affects of non-compositional factors that otherwise would affect identifying constituents of the material.

8 Claims, 1 Drawing Sheet

METHOD AND AN APPARATUS FOR ANALYZING A MATERIAL

The present invention relates to a method and an apparatus for analysing a material produced in the minerals industry to obtain information on the composition, type, or form of the material.

UK patent application GB 2083618 in the name of Outokumpu Oy describes a method and apparatus for analysing ore which is based on the use of two sources of gamma radiation each having different levels of energy. In accordance with the disclosure in the UK patent application, lumps/particles of ore are allowed to fall, one by one, past an assembly which comprises two pairs of sources of gamma radiation and an energy dispersive detector. The gamma radiation sources and the detector are positioned so that the detector receives back-scattered radiation. The passage on column 1 lines 99–113 describes that:

"Thus the essential feature of the invention is that a piece of rock or other ore sample is irradiated by means of two γ-ray sources each having a different intensity of energy. The energy of one is selected so that the Compton effect is predominant. The energy of the other is selected so that the photoelectric effect and the Compton effect compete with each other. The photoelectric effect is strongly dependent on the ordinal number of the element (i.e. its atomic number), whereas the Compton effect is independent of the ordinal number. By measuring the ratio of the intensities of these two scatters having different levels of energy, a quantity is obtained which represents the proportion of heavy elements in the rock."

Accordingly, the UK patent application relies on dual energy gamma radiation to determine the proportion of heavy elements in a lump/particle of ore and this information provides a basis to distinguish valuable ore from gangue.

An object of the present invention is to provide an improved method and apparatus for analysing a feed material produced in the minerals industry.

According to the present invention there is provided a method of analysing a material produced in the minerals industry which comprises the following steps:
  i. directing x-rays at different photon energies onto the material;
  ii. detecting x-rays transmitted through the material;
  iii. processing data relating to the detected x-rays of step (ii) obtained at the different photon energies to minimise the effects of non-compositional factors on the data and thereby to obtain from the processed data information on the composition, type, or form of the material.

The term "material" is understood herein to mean any material produced in the minerals industry, including, but not limited to, ores, minerals, or fossil fuels.

The material may be in an as-mined or in a processed form. For example, depending on the particular mineral deposit, the material may be in the form of, but not limited to, particles, lumps, fines, rocks, conglomerates, agglomerates, or aggregates.

The term "analysing" is understood herein in the broadest context and includes, but is not limited to, analysing a material for the purpose of detecting the presence of particular constituents of the material, identifying/measuring the constituents of the material, and discriminating between different constituents of the material.

The term "non-compositional factors" is understood herein to include factors such as the density and/or the thickness of a material which, together with the composition of the material, affect the absorption/transmission of x-rays that are incident on the material.

The present invention is based on the realisation that there is a wide range of applications in the minerals industry in which multiple (particularly dual) energy x-ray analysis can be used to minimise the effects of non-compositional factors on data generated in x-ray analysis of a material, which factors would otherwise make it difficult to obtain information on the composition, type, or form of the material by means of analysis of that data. The technique of dual energy x-ray analysis is based on processing data of detected transmitted x-rays obtained at different photon energies. Such processing makes it possible to minimise the effects of non-compositional factors on the detected data so that the detected data provides clearer information on the composition, type, or form of the material.

The range of applications for multiple energy x-ray analysis in the mineral industry include, but is not limited to, sorting material on the basis of composition, type, or form. One, although by no means the only, application of interest to the applicant is sorting contaminant particulate material and coal. Another application of interest to the applicant is sorting iron ore rocks on the basis of the grade of iron in the rocks.

In the context of sorting a material based on composition, type, or form, it is preferred that the method further comprises step (iv) of identifying a constituent of the material on the basis of composition, type, or form.

It is preferred that the method further comprises step (v) of separating the identified constituent from the material.

In particular, according to the present invention there is provided a method of sorting a material produced in the minerals industry which comprises the steps of:
  i. feeding a stream of the material through a gap between a source of x-rays and a detector of x-rays;
  ii. operating the x-ray source to direct x-rays at different photon energies towards the x-ray detector;
  iii. operating the detector to detect x-rays received from the x-ray source to generate data for each section of the stream of the material that passes through the gap;
  iv. identifying a constituent of the material by processing the data to minimise the effects of non-compositional factors relating to the material that otherwise would affect the identification of the constituent to thereby detect the constituent; and
  v. separating the constituent from the material.

In one particular application of the present invention it is preferred that the material comprises coal and a contaminant.

The term "contaminant" is understood herein to mean a material that is not regarded as a valuable product that is mixed with a valuable material, such as coal.

It is noted that the constituent may be a valuable material and not a contaminant.

The x-ray source may comprise two or more separate x-ray tubes operating at different voltages.

With such an arrangement, the x-ray detector may comprise two or more separate arrays of x-ray detectors.

Alternatively, the x-ray source may comprise a single x-ray tube operating at a selected voltage.

With such an arrangement, the x-ray detector may comprise two or more separate arrays of x-ray detectors. There may be one or more filtering means associated with each detector array.

For example, the separate arrays of the x-ray detectors may be aligned so that x-rays transmitted through the material are detected by a first array and thereafter by a second array. With such an arrangement, the first array acts as a filtering means for the second array.

It is preferred that the first array absorbs and detects low energy x-rays and that the second array absorbs and detects higher energy x-rays.

Alternatively, the x-ray source may comprise a single x-ray tube operating at a modulated voltage.

With such an arrangement, the x-ray detector may comprise a single detector array.

It is preferred that the maximum operating voltage of the x-ray source be less than 300 kV.

It is preferred particularly that the maximum operating voltage of the x-ray source be less than 200 kV.

The constituent separation step (iv) may comprise discharging the material from the end of a conveyor belt and selectively operating a constituent removal system to separate the detected constituent from the material in response to identification of the constituent in the data processing step (iv).

It is preferred that the contaminant removal system be based on the use of air or any other suitable fluid to displace the constituent from a path of movement.

According to the present invention there is also provided an apparatus for analysing a material produced in the minerals industry which comprises:

i. an x-ray transmission analysis system for directing x-rays at different photon energies onto the material and detecting x-rays transmitted through the material; and ii. a means for processing the data generated by the x-ray transmission system to minimise the effects of non-compositional factors on the data to obtain from the processed data information on the composition, type, or form of the material.

It is preferred that the processing means be adapted to produce x-ray images of the material at each photon energy.

The term "image" is understood herein to mean an image constructed from a time sequence of collected detector array measurements. The image may be stored electronically and/or presented visually.

It is preferred particularly that the processing means be adapted to produce a combined image of each of the different photon energy images which has enhanced contrast between constituents of the material.

In the context of sorting a material based on composition, type, or form, it is preferred that the apparatus comprises a means for identifying a constituent of the material based on composition, type, or form.

The material may be any suitable material. By way of example, the material may be run-of-mine coal or iron ore.

It is also preferred that the apparatus comprises a means for separating the identified constituent from the material.

The means for separating the constituent may be any suitable means.

In particular, according to the present invention there is provided an apparatus for sorting a material produced in the minerals industry to separate a contaminant from the remainder of the material which comprises:

i. an x-ray transmission system for transmitting x-rays through a stream of the material and generating two x-ray images at different photon energies of each section of the stream of the material;

ii. a means for processing the images to produce a combined image which has enhanced contrast between the contaminant and the remainder of the material to enable detection of the contaminant; and iii. a means for separating the contaminant from the remainder of the material.

In one particular, although by no means exclusive, application of the present invention it is preferred that the material comprises coal.

It is preferred that the x-ray transmission system comprises a source of x-rays and a detector of x-rays transmitted through the material.

With such an arrangement, it is preferred that the apparatus further comprises a means for feeding the stream of the material through a gap between the x-ray source and the x-ray detector.

The feed means may comprise a conveyor belt assembly extending through the gap.

Alternatively, the feed means may comprise a conveyor belt assembly arranged to discharge the stream of the material so that the trajectory of the discharged material extends through the gap.

The x-ray source may comprise two or more separate x-ray tubes adapted to be operated at different voltages.

With such an arrangement, the x-ray detector may comprise two or more separate arrays of x-ray detectors.

Alternatively, the x-ray source may comprise a single x-ray tube adapted to be operated at a selected voltage.

With such an arrangement, the x-ray detector may comprise two or more separate arrays of x-ray detectors with the arrays having different filtering means.

For example, the separate arrays of the x-ray detectors may be aligned so that x-rays transmitted through the material are detected by a first array and thereafter by a second array. With such an arrangement, the first array acts as a filtering means for the second array.

It is preferred that the first array absorbs and detects low energy x-rays and that the second array absorbs and detects higher energy x-rays.

Alternatively, the x-ray source may comprise a single x-ray tube adapted to be operated at a modulated voltage.

With such an arrangement, the x-ray detector may comprise a single detector array.

It is preferred that the maximum operating voltage of the x-ray source be less than 300 kV.

It is preferred particularly that the maximum operating voltage of the x-ray source be less than 200 kV.

The method and the apparatus of the present invention as described above has a number of advantages over the arrangement disclosed in UK patent application GB2083618. For example, the use of transmitted rather than back-scattered radiation enables more representative analysis. Furthermore, the generation of an image enables the position of a selected constituent/contaminant to be accurately determined and this provides an effective basis to subsequently separate the constituent/contaminant. In addition, the use of image processing makes it possible to determine the shape of a constituent/contaminant and therefore separation can be achieved on this basis. Furthermore, the present invention can operate at significantly lower energy levels than the levels of 300–1500 kV reported in the UK patent specification. Furthermore, the present invention is not restricted to the use of complex energy dispersive detection.

The present invention is based on experimental work carried out by the applicant which indicates that dual energy x-ray image analysis of run-of-mine coal which contains contaminants can be an effective basis for sorting the coal on the basis of composition, type, or form. The present invention is also based on experimental work carried out by the applicant on iron ore.

In particular, the applicant has found in experimental work that dual energy x-ray image analysis has the advantage of being able to distinguish contaminants from coal and to be able to distinguish iron ore rocks on the basis of the grade of iron.

The applicant has found in the experimental work, in relation to coal that dual energy x-ray analysis has the additional advantages of being able to:
i. distinguish contaminants from any shale that is present in the run of mine coal; and
ii. detect fine contaminants.

In the experimental work in relation to coal the applicant selected two x-ray images of a 65 mm bed of a sample of a run-of-mine coal at 50 kV and 85 kV voltage settings. The images were obtained by directing x-rays onto the bed and detecting x-rays transmitted through the coal by means of x-ray detectors positioned beneath the bed.

The images had a high degree of coal bed variation, some shale, and contaminants.

The images were processed by two separate computer programs based on different algorithms to produce, in each case, a combined image of the two original images that enhanced differences in composition of the coal and the contaminants and minimised differences in other variables such as density and the bed thickness.

The original and the combined images were further processed to obtain profiles along the same line in all of the images. The line was chosen to pass through the coal bed, some shale, and the contaminants. The profiles along the lines are shown in FIG. 1.

With reference to the figure, the two upper profiles are the profiles obtained from the original images at 50 kV and 85 kV energy levels. It can be seen from these profiles that there are significant variations in signal level across the profiles and these significant variations makes it difficult to discriminate on the basis of composition. These significant variations are the result of the effect of compositional factors and non-compositional factors such as density and thickness on absorption/transmission of x-rays.

The lower two profiles in the figure are the profiles obtained from the combined images using methods 1 and 2, respectively. It can be seen that the effect of the methods is to reduce significantly the variations in signal level across the profiles by minimising the effect of non-compositional factors on the data with the result that the variations in signal level are attributable to composition. It can be seen that both processing methods enhanced the image of the contaminants above that of the coal bed and the shale and, as a consequence, the combined images produced by both processing methods provided a basis to distinguish contaminants from valuable coal and shale.

The applicant carried out experimental work to investigate the feasibility of separating detected contaminants from run-of-mine coal.

The experimental work was carried under conditions that were designed to simulate sorting conditions associated with contaminants removal from coal which is transported via a conveyor operating at a feed rate of 600 tph at a belt speed of 3.7 to 4 m/s.

The experimental work was carried out on a test-rig which comprised a hopper having an adjustable outlet gate which supplied run-of-mine coal which contained contaminants onto a variable speed conveyor belt arranged to form a 220 mm wide stream. The conveyor belt discharged the stream in a trajectory that cleared a splitter plate so that acceptable coal was chanelled into an "accept" bin on one side of the splitter plate.

The test rig also included a blast array that was positioned adjacent to the trajectory to separate contaminants from the coal. The following blast arrays were tested:
i. 3 blast valves connected via hydraulic hosing to nozzles in line, at 50 mm centres between the nozzles, and with each nozzle being 12 mm ID round flattened into a fan profile;
ii. 3 blast valves connected via hydraulic hosing to nozzles in line, at 50 mm centres between the nozzles, and with each nozzle being 12 mm ID round;
iii. 5 blast valves connected via hydraulic hosing to 12 mm ID round nozzles at 25 mm spacing between centres of the nozzles; and
iv. 1 1.5 inch 3-way blast valve with a 32 mm ID round nozzle.

The blast arrays were connected via a manifold to an air reservoir of 700 kPa for most of the experimental work and for 400 kPa for the remainder of the test work.

The test rig also included a detector system for detecting contaminants in the stream of coal which was coupled to the blast arrays to activate selectively the blast arrays to displace detected contaminants from the trajectory.

The experimental work on the test rig established that contaminants could be removed effectively from an airborne stream of run-of-mine coal presented at conveyor belt speeds of up to 4 m/s without significant loss of coal.

Many modifications may be made to the preferred embodiment of the present invention without departing from the spirit and scope of the present invention.

In this regard, whilst the above-described experimental work relates to run-of-mine coal, the present invention is not so limited and extends generally to materials produced in the minerals industry.

Furthermore, whilst the above-described experimental work relates to processing feed material in which the valuable material is the bulk of the feed material, the present invention is not so limited in scope and extends to situations in which the bulk of the feed material is gangue.

What is claimed is:

1. A method of sorting a material produced in the minerals industry which comprises the steps of:
i. feeding a stream of the material through a gap between a single x-ray tube operating at a selected voltage and two or more separate arrays of x-ray detectors;
ii. operating the x-ray tube and directing x-rays of different photon energies towards the x-ray detectors;
iii. operating the detectors and detecting x-rays received from the x-ray tube and generating data of detected transmitted x-rays obtained at different photon energies for each section of the stream of the material that passes through the gap;
iv. identifying a constituent of the material by processing the data of detected transmitted x-rays obtained at different photon energies to minimise the effects of non-compositional factors relating to the material that otherwise would affect the identification of the constituent to thereby detect the constituent; and
v. separating the constituent from the material.

2. The method defined claim 1 wherein the constituent is a contaminant and the separation step (iv) comprises discharging the material from the end of a conveyor belt and selectively operating a contaminant removal system to separate the contaminant from the material.

3. An apparatus for sorting a material produced in the minerals industry to separate a contaminant from the remainder of the material which comprises:

i. an x-ray transmission analysis system for directing x-rays at different photon energies onto the material and detecting x-rays transmitted through the material, the system comprising a single x-ray tube adapted to operate at a selected voltage and two or more separate arrays of x-ray detectors; and ii. a means for processing the data generated by the x-ray transmission system to minimise the effects of non-compositional factors on the data to obtain from the processed data information on the composition, type, or form of the material.

4. The apparatus defined in claim 3 wherein the processing means comprises a means to produce x-ray images of the material at each photon energy.

5. The apparatus defined in claim 4 wherein the processing means comprises a means to produce a combined image of each of the different photon energy images which has enhanced contrast between constituents of the material.

6. The apparatus defined in claim 1 wherein the apparatus further comprises a means for feeding the stream of the material through a gap between the x-ray tube and the x-ray detectors.

7. The apparatus defined in claim 6 wherein the feed means comprises a conveyor belt assembly extending through the gap.

8. The apparatus defined in claim 6 wherein the feed means comprises a conveyor belt assembly arranged to discharge the stream of the material so that the trajectory of the discharged material extends through the gap.

* * * * *